United States Patent [19]
Hicken

[11] Patent Number: 5,184,626
[45] Date of Patent: Feb. 9, 1993

[54] BRUSH OVERLAY PAP SMEAR

[76] Inventor: William J. Hicken, 2205 Eastlake Rd., Timonium, Md. 21093

[21] Appl. No.: 703,732

[22] Filed: May 21, 1991

[51] Int. Cl.$^5$ ............................................. A61B 10/00
[52] U.S. Cl. ...................................... 128/756; 128/757
[58] Field of Search .................. 128/749, 756–759; 424/3; 435/1

[56] References Cited

U.S. PATENT DOCUMENTS

| | | | |
|---|---|---|---|
| 3,554,185 | 2/1974 | Kohl | 128/757 |
| 3,640,268 | 2/1972 | Davis | 128/757 |
| 3,664,328 | 5/1972 | Moyle et al. | 128/756 |
| 4,054,127 | 10/1977 | Milan et al. | 128/757 |
| 4,127,113 | 11/1978 | Nollan | 128/756 |
| 4,227,537 | 10/1980 | Suciu et al. | 128/756 |
| 4,620,548 | 11/1986 | Hasselbrack | 128/758 |

Primary Examiner—Max Hindenburg
Attorney, Agent, or Firm—Morton J. Rosenberg; David I. Klein

[57] ABSTRACT

A brush overlay Pap smear method is provided for providing a single cytological sample representing specimens for two or more sites. An exocervical sample (20) is transferred from a scraper (40) to an end portion (16) of a surface (14) of a microscope slide (10). Subsequently, an endocervical sample is combined with the exocervical sample (20) and distributed across the surface (14) of slide (10) to provide a substantially uniform distribution of the combined samples into a substantially uniform film (22) on the surface (14) of slide (10). In an alternate embodiment, the application of the exocervical sample is preceded by the application of exfoliated cells obtained from the posterior fornix of the vagina, the exocervical sample being applied to the exfoliated cell sample (30) to form a combined sample (32). As in the first embodiment, an endocervical sample is combined with the combined sample pool (2) and substantially simultaneously distributed across the surface (14) of slide (10) by a rotative displacement of the cytological brush (50) on the surface (14) of slide (10).

7 Claims, 2 Drawing Sheets

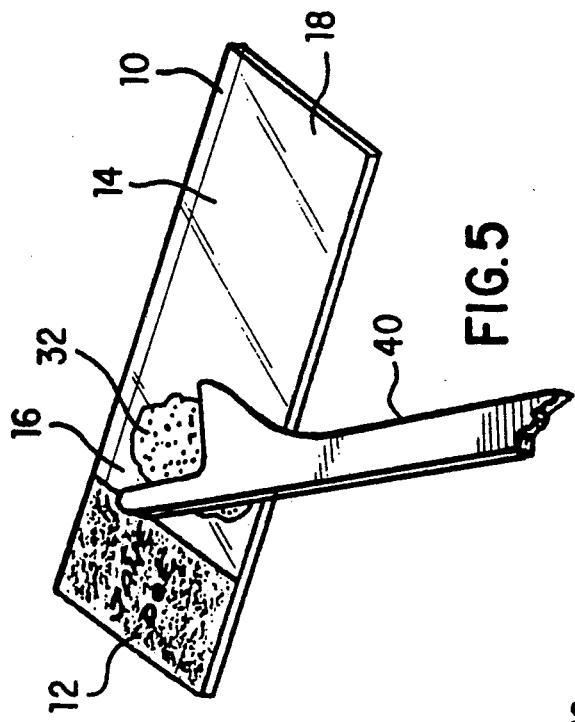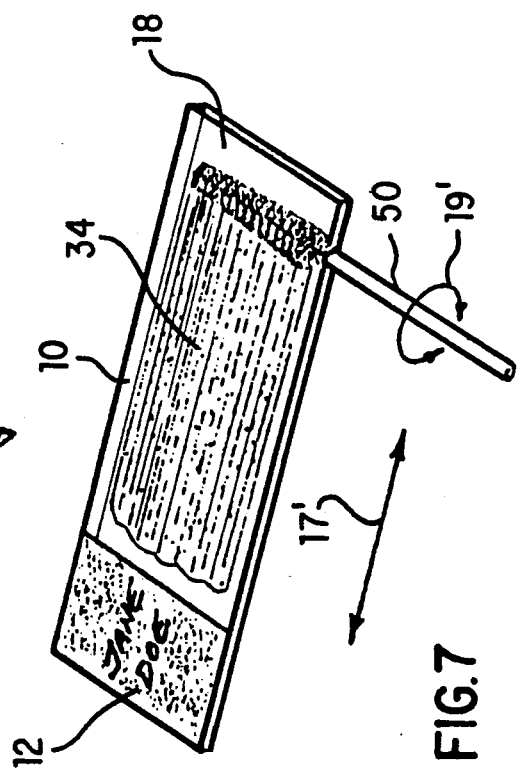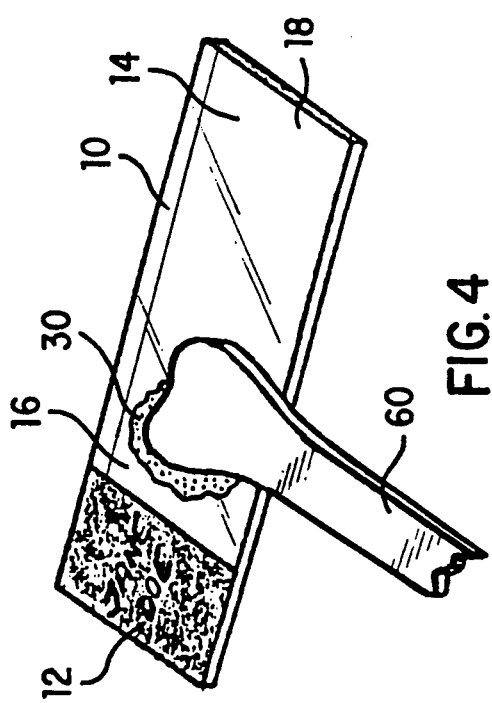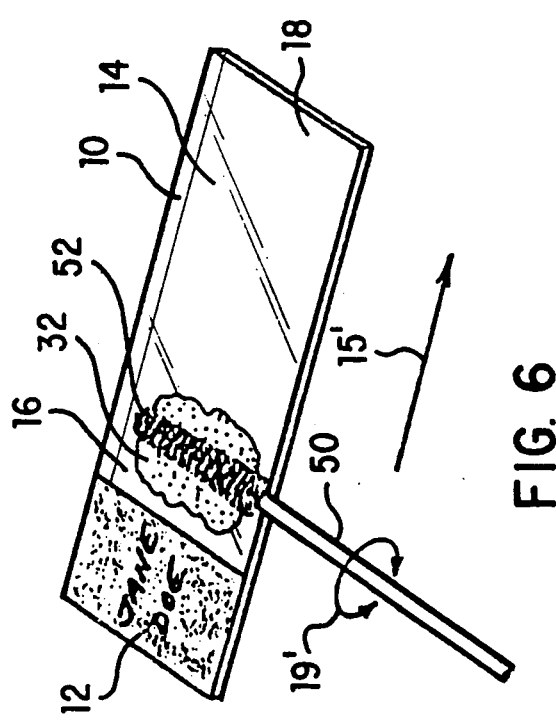

BRUSH OVERLAY PAP SMEAR

BACKGROUND OF THE INVENTION

1. Field of the Invention

This invention directs itself to a method of preparing a Pap smear. In particular, this invention directs itself to a method for combining cytological samples from multiple sites into a single specimen. More in particular, this invention directs itself to a brush overlay method wherein the application of the final cytological sample is combined with samples which have been previously obtained and applied to a slide, wherein the sample contained within the interstices of the cytological brush are simultaneously combined with the other samples and distributed uniformly across the surface of the slide. Further, the means for combining and distributing the multiple samples utilizes a light downward pressure, normal to the surface of the slide, while simultaneously rotatively displacing the cytological brush in a single direction, or alternately the brush is reciprocated back and forth across the surface of the slide.

2. Prior Art

Devices for collecting cytological samples, and methods of preparing Pap smears are well known in the art. The best prior art known to the Applicant include U.S. Pat. Nos. 3,640,268; 3,881,464; 4,127,113; 4,227,537; 4,620,548; 4,754,764; 4,759,376; 4,762,133; 4,873,992; and, 4,936,312.

Some prior art systems, such as that shown in U.S. Pat. No. 4,754,764 are directed to cervical cytology devices for simultaneously sampling both the exocervical and endocervical areas. However, the device is formed as a two-part structure, such that subsequent to sampling the two parts are separated, and the cells collected by each portion are disposed on separate slides. Thus, while the collection of the cytological samples is made more efficient, the laboratory must still examine two separate specimens. The two slides must be separately screened and evaluated by the pathologist, thereby essentially doubling the cost to the patient.

In other prior art systems, such as that disclosed in U.S. Pat. Nos. 4,127,113; 4,227,537; and 4,759,376 cytological brush systems are disclosed. While such prior art systems disclose the transfer of the cytological sample obtained with the brush by rotating the brush and streaking it longitudinally across the surface of the slide, such is for the distribution of a single sample. Therefore, each of these systems is intended to obtain an endocervical sample for application to a slide, but they do not disclose or suggest the method of the instant invention.

Other prior art systems, such as disclosed in U.S. Pat. No. 4,620,548 are directed to devices for collecting cytological samples from multiple sites. While such systems disclose the combination of two samples, one obtained by aspiration, and the other by means of a scraper, the samples are combined and distributed by a smearing action. In such systems, the aspirated sample is pooled onto a slide followed by the rubbing of the scraped sample therewith. The combined sample is then spread across the surface of the slide by the longitudinal displacement of a cylindrical surface portion of the instrument. However, such mixing and distribution of the sample does not provide the necessary uniformity for accurate microscopic evaluation, as achieved by the method of the instant invention. The uniformity of the sample is critically important to the accuracy of the laboratory evaluation. If an unsatisfactory slide results, then the sample taking procedure must be repeated. Further, this prior art technique does not disclose or suggest a method by which more than two samples can be combined to provide a single slide specimen.

SUMMARY OF THE INVENTION

A method for preparing a cytological smear is provided. First, an initial cytological sample is applied to a portion of a slide, adjacent a first end thereof. Subsequently, a final cytological sample is applied from a substantially cylindrically shaped sampling brush to the slide portion having the initial cytological sample thereon. The final sample is applied in overlaying relationship with the initial sample. The cylindrically shaped sampling brush is then rotatively displaced in a first direction, from the slide portion adjacent the first end to a second end of the slide, for distributing the cytological samples thereon. This last step is repeated until a uniform cytological sample distribution is obtained.

BRIEF DESCRIPTION OF THE DRAWINGS

FIG. 4 is a perspective view of an alternate method wherein a cytological sample is applied from a scraper to a microscope slide;

FIG. 5 is a perspective view of an additional cytological sample being applied to the microscope slide, in overlaying relationship with the initial cytological sample;

FIG. 6 is a perspective view of a final cytological sample being applied from a cytological brush to the combined previously applied cytological samples disposed on a microscope slide; and, FIG. 7 is a perspective view of the combined cytological samples being distributed on the surface of a microscope slide.

DESCRIPTION OF THE PREFERRED EMBODIMENTS

Referring to FIGS. 1-3, or FIGS. 4-7, there is shown embodiments of the brush overlay Pap smear system for preparing a cytological sample for microscopic examination. In overall concept, the brush overlay Pap smear system provides a method whereby cytological samples from multiple sites can be examined simultaneously for atypical cells. This method for combining samples from multiple sites improves the efficiency of Pap smear evaluation techniques. Further, the unique method of the overlay system accommodates different sample selection criteria, as a function of the age group of the patient. Still further, the method of the inventive concept provides an improvement of the sample distribution on the slide of samples taken from the Ayres type scraper 40.

Figure 1:
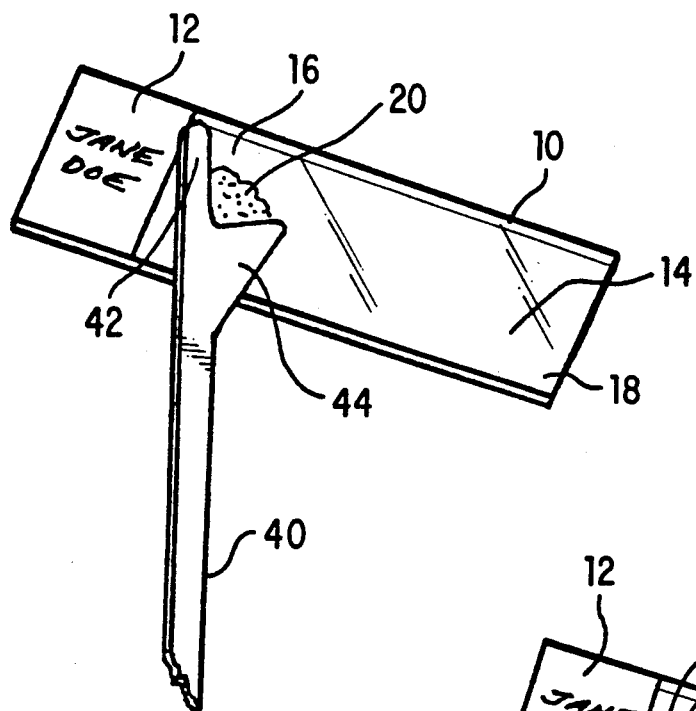
FIG. 1 is a perspective view of the application of a cytological sample from a scraper to the microscope slide.
Figure 2:
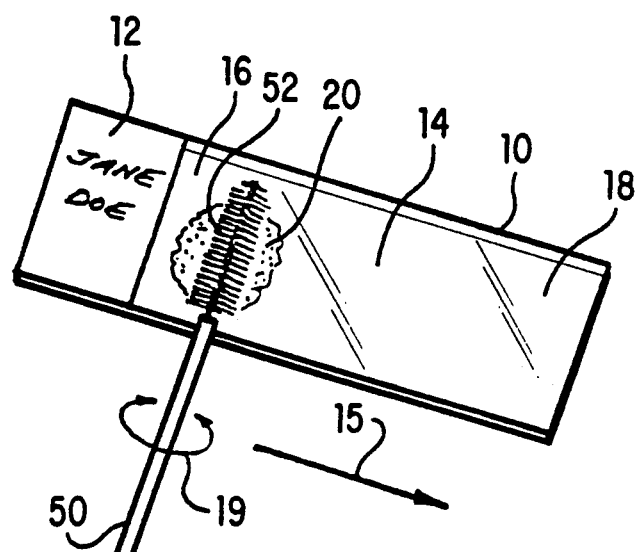
FIG. 2 is a perspective view of the application of a cytological sample from a cytological brush to a microscope slide, in overlaying relationship with a sample already thereon.
Figure 3:
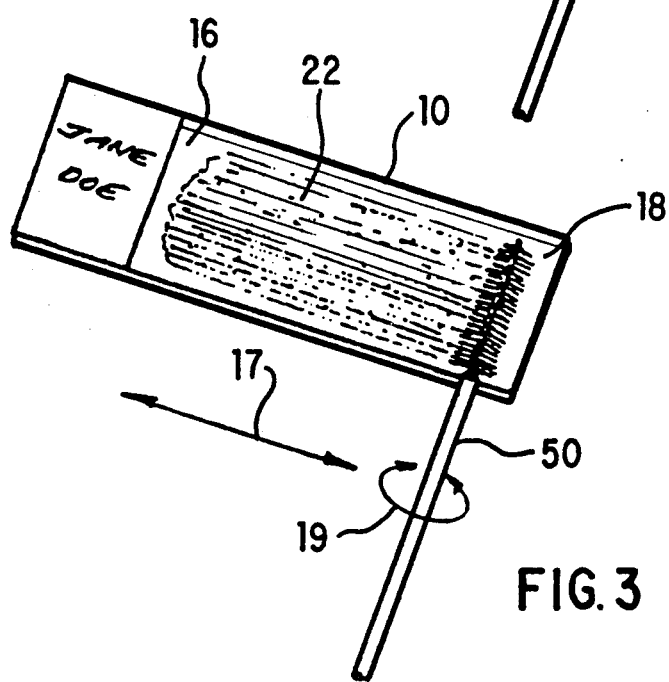
FIG. 3 is a perspective view of the combined cytological samples being distributed over the surface of a microscope slide.

For purposes of defining and clarifying the general method of the brush overlay pap smear of FIGS. 1-3, it is understood that the Ayres type scraper 40 has a portion 42 which is inserted into the endocervical canal until the blade portion 44 abuts the exocervix area. The instrument is subsequently rotated about the axis defined by the end portion 42 such that the blade portion 44 scrapes the entire circumferential exocervix area. The sample collected on the blade portion 44 of the scraper 40 is transferred to the microscope slide 10. The microscope slide 10 may be a standard glass slide having a frosted portion 12 for carrying identifying indicia thereon, and a smooth flat surface 14 extending from the frosted region 12 to the distal end of the slide 18. The cytological sample 20 obtained from the scraper 40 is deposited on the slide surface 14 at a portion 16 adjacent the frosted portion 12. The cytological sample 20 is applied to the glass slide by a gentle rubbing of the scraper thereon.

Subsequently, an endocervical brush 50 is inserted into the endocervical canal, and rotated in order to accumulate a sample of cells therefrom. Upon removal from the patient, the bristle portion of the brush 50, having a cylindrically shaped contour, is placed on the surface 14 of microscope slide 10 in overlaying relationship with the exocervical sample 20 previously placed thereon. The brush is then rotated through multiple 360° rotations, indicated by directional arrow 19, while being displaced from the portion 16, adjacent the frosted end portion 12 toward the distal end 18, in the direction indicated by directional arrow 15, shown in FIG. 2. This step may then be repeated until the exocervical and endocervical samples have been combined to form a film 22 which is uniformly distributed over the surface 14 of microscope slide 10. It has been empirically found that two or three repetitions are all that is required to accomplish a uniform distribution. Alternately, as shown in FIG. 3, the brush 50 may be rotated back and forth between portions 16 and 18 of microscope slide 10 as indicated by the direction arrows 17 and 19, to uniformly distribute the collected samples.

Immediately following the distribution of the samples by the rotative displacement of the brush 50, the slide is sprayed with a cytofixative, as is well known in the art. Thus, the exocervical and endocervical samples are combined, in overlaying relationship to provide a single slide for examination, as opposed to the prior art system of preparing separate slides, or slides having multiple defined portions for receiving a single particular sample thereon. It can therefore be seen that the brush overlay Pap smear method reduces the laboratory steps necessary to screen the Pap smear, as there is only a single smear, as opposed to multiple slides or a single slide containing multiple smears, each requiring separate screening. The brush overlay Pap smear method further provides a substantially uniform mixing of the multiple samples and substantially simultaneously distributes the samples uniformly across the slide. The uniformity of the sample distribution is critically important to the accuracy and efficiency of the cytological evaluation. This novel method substantially prevents the formation of large blobs, multiple streaks, or spots of material, whose evaluation is difficult or impossible, thereby eliminating the need for repeating the sample taking procedure to obtain a satisfactory smear.

While the screening method just described is typically considered adequate for younger women, it is desirable to include a sample from the "vaginal pool", the posterior fornix of the vagina, in women who are peri-menopausal and post-menopausal. To accommodate this requirement, prior art techniques collected three separate samples, disposing them on separate slides, or separate portions of a single slide, requiring separate evaluations of each.

Referring now to FIGS. 4–7, there is shown the method by which samples from the vaginal pool, exocervical area, and the endocervical canal are combined to form a single Pap smear, requiring only a single evaluation. As shown in FIG. 4, the vaginal pool sample 30 is transferred from the scraper 60 to the surface 14 of slide 10, on the portion 16 which is adjacent the frosted end portion 12. The vaginal pool sample 30 is dabbed onto the slide from the scraper 60 to deposit the sample thereon. Next, as shown in FIG. 5, the exocervical sample, which was collected by means of the Ayres type scraper 40, is deposited on the slide 10 in overlaying relationship with the sample 30 to form a combined sample 32. The exocervical sample is combined with the vaginal pool sample, but not spread across the slide. Finally, as shown in FIG. 6, the endocervical sample obtained with the cytological brush 50 is applied to the surface 14 by rotative displacement of the brush 50 across the surface 14 of slide 10. The bristles 52 of the brush 50 are disposed on the sample 32, and simultaneously spread the sample 32 while combining the endocervical sample contained within the interstices of the bristles 52 therewith.

As previously stated, the brush 50 is rotatively displaced from the portion 16 across the slide to the end portion 18, in the direction indicated by direction arrow 15' of FIG. 6. This step is repeated several times until the sample is uniformly spread across the surface, which also affords the mixing of the three cytological samples in a substantially uniform distribution 34. Alternately, the cytological brush 50 may be rotatively displaced back and forth, as indicated by directional arrow 17' of FIG. 7, to uniformly distribute and mix the combined cytological samples to form a uniform film 34.

Immediately subsequent to forming the uniform film 34, the slide is fixed with a spray cytofixative, as well known in the art. Thus, here again, multiple diagnostic screenings of slide, for a single patient, is eliminated, allowing the pathologist to screen a single slide for early detection of cancer.

In reviewing the method, FIGS. 1–3 are directed to the overlay method of obtaining a Pap smear for premenopausal women. An exocervical sample is first obtained and transferred to a surface portion 16 of a microscope slide surface 14 by a light rubbing action to remove the cytological sample from the scraper 40. The endocervical sample, which is contained within the interstices of the bristles 52 of the cytological brush 50, is transferred to the microscope slide 10 and mixed with the exocervical sample 20, substantially simultaneously, by disposing the bristles 52 on the slide surface portion 16 overlaying the sample 20, and simultaneously applying a light pressure to the brush 50 in a downward direction normal to the surface 14 of slide 10, while rotating the brush, as indicated by the direction arrow 19 and displacing it from the portion 16 to the distal end 18 of slide 10, indicated by direction arrow 15. This step may be repeated two to three times, or alternately, the rotation and displacement of the brush 50 may be reversed upon reaching the distal end 18. The rotative direction is reversed and the displacement proceeds in a direction from the distal end 18 to the portion 16, the procedure being repeated until a uniform distribution is obtained. Immediately subsequent, a spray cytofixative is applied to the slide to prevent any drying of the cells, which would otherwise distort the cells and thereby interfere with the cytological evaluation.

In peri-menopausal and post-menopausal women, it is desirable to examine exfoliated cells from the posterior fornix of the vagina, in addition to exocervical and endocervical samples. The brush overlay Pap smear method, as shown in FIGS. 4-7, is adaptable to the diagnostic regimen of this group of patients. the vaginal pool sample 30 is transferred from the scraper 60 to the slide surface portion 16 by a light rubbing action. Similarly, the exocervical scraping is combined with the vaginal pool sample by lightly rubbing the scraper 40 in the vaginal pool sample, forming a combined cytological sample 32. Lastly, the cytological brush having the endocervical sample disposed within the interstices of the bristles 52 is gently pressed against the surface of the slide 14 on the end portion 16, in overlaying relationship with the combined cytological sample 32. While applying a light pressure to the brush, in a downward direction normal to the surface 14 of slide 10, the brush is rotatively displaced along the surface of the slide, in a direction indicated by the direction arrow 15', shown in FIG. 6. The combination of the downward pressure of the brush against the surface 14 of slide 10, and the rotation of the bristles through the cytological sample 32, substantially simultaneously mixes the vaginal pool, exocervical, and endocervical samples while distributing the combined sample in a uniform distribution 34 across the slide. The cytological brush 50 may be rotated in a single direction to displace the brush from the portion 16 to the distal end 18, for several repetitions, or reversibly rotated so as to reciprocate back and forth between the end portions 16 and 18 of surface 14, to form a uniform film 34 thereon.

Although this invention has been described in connection with specific forms and embodiments thereof, it will be appreciated that various modifications other than those discussed above may be resorted to without departing from the spirit or scope of the invention. For example, equivalent steps may be substituted for those specifically shown and described, certain features may be used independently of other features, and in certain cases, particular steps or elements may be reversed or interposed, all without departing from the spirit or scope of the invention as defined in the appended claims.

What is claimed is:

1. A method for preparing a cytological smear, comprising the steps of:
   a. applying an exocervical cytological sample with a spatula to a portion of a slide adjacent a first end thereof;
   b. applying a endocervical cytological sample from a substantially cylindrically shaped sampling brush to said slide portion slide, said final sample being applied in overlaying relationship with said exocervical sample;
   c. rotatively displacing said sampling brush in a first direction from said slide portion adjacent said first end to a second end of said slide followed by rotatively displacing said brush in a second direction, said second direction being opposite said first direction for distributing said cytological samples thereon, said rotative displacement being substantially simultaneous with application of a predetermined pressure between said sampling brush and said slide as said brush is rotatively displaced;
   d. repeating step c. until a uniform cytological sample distribution is obtained; and,
   e. applying a cytofixative to said uniform cytological distribution on said slide.

2. The method for preparing a cytological smear as recited in claim 1 where said step of applying said exocervical cytological sample is preceded by the step of applying a vaginal pool cytological sample to said slide portion adjacent said first end, said exocervical cytological sample being applied in overlaying relationship with said vaginal pool cytological sample.

3. The method for preparing a cytological smear as recited in claim 2 wherein said step of applying said vaginal pool cytological sample includes applying said vaginal pool sample with a spatula.

4. A method for preparing a cytological smear, comprising the steps of:
   a. applying an initial cytological sample with a spatula to a portion of a slide adjacent a first end thereof;
   b. applying a final cytological sample from a substantially cylindrical shaped sampling brush to said slide portion slide, said final sample being applied in overlaying relationship with said initial sample;
   c. rotatively displacing said sampling brush in a first direction from said slide portion adjacent said first end to a second end of said slide followed by rotatively displacing said brush in a second direction, said second direction being opposite said first direction for distributing said cytological samples thereon, said rotative displacement being substantially simultaneous with application of a predetermined pressure between said sampling brush and said slide as said brush is rotatively displaced;
   d. repeating step c. until a uniform cytological sample distribution is obtained; and,
   e. applying a cytofixative to said uniform cytological distribution on said slide.

5. The method for preparing a cytological smear as recited in claim 4 where said step of applying said final cytological sample is preceded by the step of applying an intermediate cytological sample to said slide portion adjacent said first end, said intermediate sample being applied in overlaying relationship with said initial sample.

6. The method for preparing a cytological smear as recited in claim 5 where said step of applying said intermediate cytological sample includes applying said intermediate sample with a spatula.

7. A method for preparing a cytological smear, comprising the steps of:
   a. applying a vaginal pool cytological sample with a spatula to a portion of a slide adjacent a first end thereof;
   b. applying an exocervical cytological sample to said slide portion adjacent said first end, said exocervical cytological sample being applied in overlaying relationship to said vaginal pool sample with a spatula;
   c. applying an endocervical cytological sample from a substantially cylindrically shaped sampling brush to said slide portion adjacent said first end, said endocervical sample being applied in overlaying relationship with both said vaginal pool and said exocervical samples;
   d. rotatively displacing said sampling brush in a first direction from said slide portion adjacent said first end to a second end of said slide followed by rotatively displacing said brush in a second direction, said second direction being opposite said first direction for distributing said cytological samples thereon, said rotative displacement being substantially simultaneous with application of a predetermined pressure between said sampling brush and said slide as said brush is rotatively displaced;

e. repeating step d. until a uniform cytological sample distribution is obtained; and, f. applying a cytofixative to said uniform cytological distribution on said slide.

* * * * *